United States Patent [19]

Salyer

[11] Patent Number: 5,171,313
[45] Date of Patent: Dec. 15, 1992

[54] TOOL DRIVER

[75] Inventor: Brian D. Salyer, Warsaw, Ind.

[73] Assignee: Othy, Inc., Warsaw, Ind.

[21] Appl. No.: 696,951

[22] Filed: May 8, 1991

[51] Int. Cl.$^5$ ................................................ A61F 5/04
[52] U.S. Cl. ...................................... 606/86; 606/99; 606/100
[58] Field of Search ....................... 606/86, 87, 88, 99, 606/100, 104, 90, 91

[56] References Cited

U.S. PATENT DOCUMENTS

| 2,437,014 | 3/1948 | Arnesen | 606/100 |
| 2,725,878 | 12/1955 | Reiter | 606/100 |
| 4,459,985 | 7/1984 | McKay | 606/100 |
| 4,987,904 | 1/1991 | Wilson | 606/86 |

Primary Examiner—Robert A. Hafer
Assistant Examiner—Michael Brown
Attorney, Agent, or Firm—Lundy & Associates

[57] ABSTRACT

A tool driver having a body with a longitudinal axis and opposite ends. A boss is positioned at one of the ends. A tool collet is positioned at the other of the ends. A plunger is positioned within a bore in the body. The body has a pair of oppositely disposed pins, at least one of the pins being movable in relation to said body in response to movement of the plunger. An actuator is positioned on and connected to the plunger. The actuator and plunger move as a unit axially of said body between an at rest position and a static position. One pin is movable between an extended position and a retracted position as the plunger and actuator move between an at rest position and a static position, whereby a tool can be positioned on the tool driver when the plunger and actuator are in their static position and held in operable position on the tool driver when the plunger and actuator are in their at rest position.

18 Claims, 3 Drawing Sheets

TOOL DRIVER

BACKGROUND OF THE INVENTION

The present invention pertains to holders for rotary tools, and more particularly pertains to a tool driver suitable for use with acetabular reamer cups or other similarly shaped tools which are secured onto a tool driver by diametrically opposed pins.

Acetabular reamer cups are surgical tools which are used to cut hemispherical cavities in pelvis bones for the insertion of artificial hip joints. Acetabular reamer cups are mounted on tool drivers, which in turn are mounted in the chuck or collet of a portable drill or flexible powered shaft. Acetabular reamer cups are separable from their tool drivers to replace or sharpen as they are used. It may be necessary to change cups during an operation, for example. Tool drivers are not inexpensive and must be cleaned and reused.

Some previous tool drivers usable with acetabular reamer cups grip the cup without the use of opposed pins by means of a flange and slot and an opposed spring-loaded ball catch, like that on a socket wrench or socket driver or other catch devices. This represents a problem in that the catch tends to trap dried blood and other debris, which is very difficult to remove during cleaning. An additional problem is that unless tolerances of cups and tool drivers are made very close, at greatly increased cost, there is considerable free play between the cup and tool driver. This increases wear and decreases the precision of the tool.

An alternative tool driver usable with acetabular cups, described in Salyer, U.S. Pat. No. 4,811,632, issued on Mar. 14, 1989, has a cam and follower mechanism which provides for axial and rotary movement of a clamp. That driver avoids many of the problems presented by the ball catch, but requires a separate locking mechanism and two handed use.

The current pin type tool drivers also cannot be disassembled easily for thorough cleaning. Additionally, they have exposed trigger mechanisms which can catch and tear a surgeon's glove and are generally cumbersome to operate.

It is therefore highly desirable to provide an improved tool driver.

It is also highly desirable to provide an improved pin type tool driver which can be easily actuated to grip and release tools, such as an acetabular reader cup.

It is also highly desirable to provide an improved pin type tool driver which can be completely disassembled for cleaning.

It is also highly desirable to provide an improved pin type tool driver which does not tend to catch bone debris.

It is also highly desirable to provide an improved pin type tool driver which can be easily joined or disjoined from an acetabular reamer cup with a single hand.

It is also highly desirable to provide an improved pin type tool driver which eliminates exposed parts which can catch and tear a surgeon's gloves, and is easily operable.

It is finally highly desirable to provide an improved pin type tool driver which meets all of the above desired features.

SUMMARY OF THE INVENTION

It is an object of the invention to provide an improved tool driver.

It is also an object of the invention to provide an improved pin type tool driver which can be easily actuated to grip and release tools, such as an acetabular reamer cup.

It is also an object of the invention to provide an improved pin type tool driver which can be completely disassembled for cleaning.

It is also an object of the invention to provide an improved pin type tool driver which does not tend to catch bone debris.

It is also an object of the invention to provide an improved pin type tool driver which can be easily joined or disjoined from an acetabular reader cup with a single hand.

It is also an object of the invention to provide an improved pin type tool driver which eliminates exposed parts which can catch and tear a surgeon's gloves, and is easily operable.

It is finally an object of the invention to provide an improved pin type tool driver which meets all of the above desired features.

In the broader aspect of the invention there is provided a tool driver having a body with a longitudinal axis and opposite ends. A boss is positioned at one of the ends. A tool collet is positioned at the other of the ends. A plunger is positioned within a bore in the body. The body has a pair of oppositely disposed pins, at least one of the pins being movable in relation to said body in response to movement of the plunger. An actuator is positioned on and connected to the plunger. The actuator and plunger move as a unit axially of said body between an at rest position and a static position. One pin is movable between an extended position and a retracted position as the plunger and actuator move between an at rest position and a static position, whereby a tool can be positioned on the tool driver when the plunger and actuator are in their static position and held in operable position on the tool driver when the plunger and actuator are in their at rest position.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
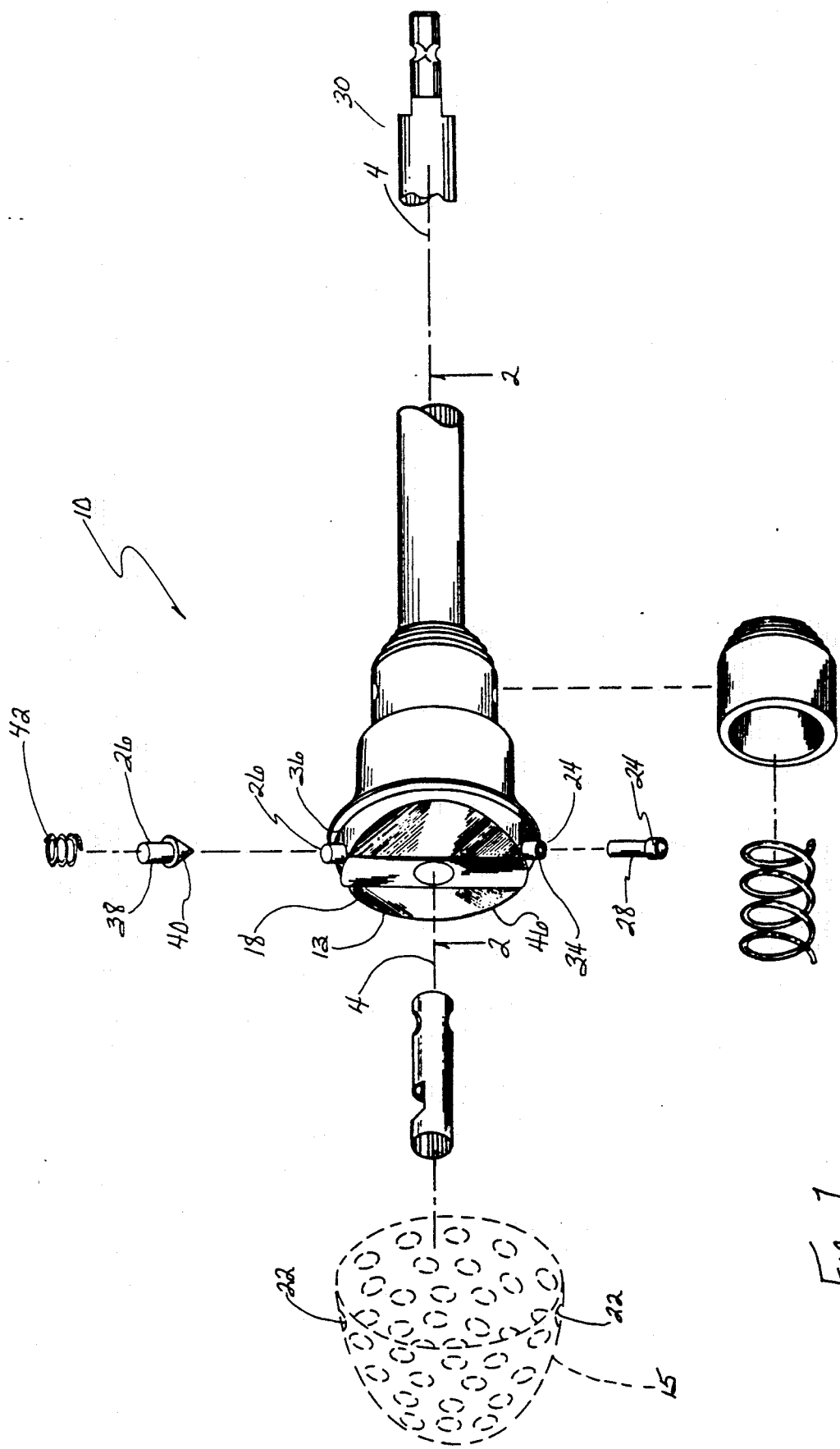
FIG. 1 is a perspective, exploded view of the tool driver of the invention.
Figure 2:
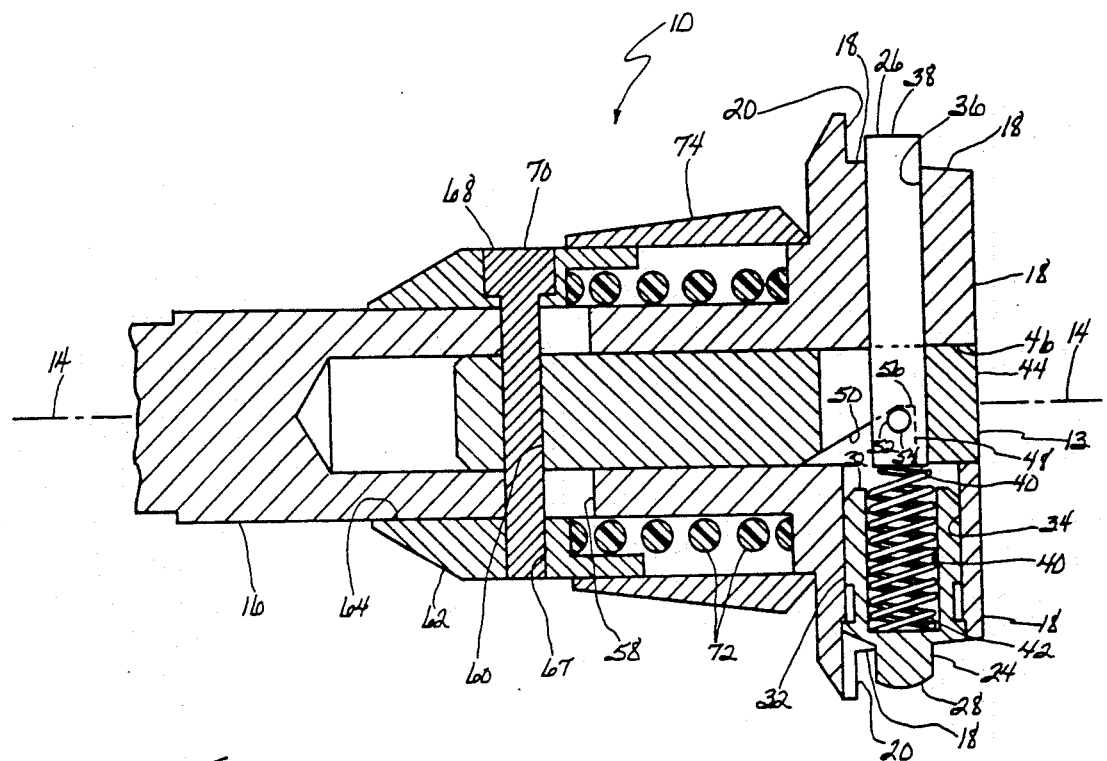
FIG. 2 is a cross-sectional view of a similar tool driver of the invention as if taken substantially along line 2—2 of FIG. 1. The action pin is in its extended position and the actuator is in its retracted position.
Figure 3:
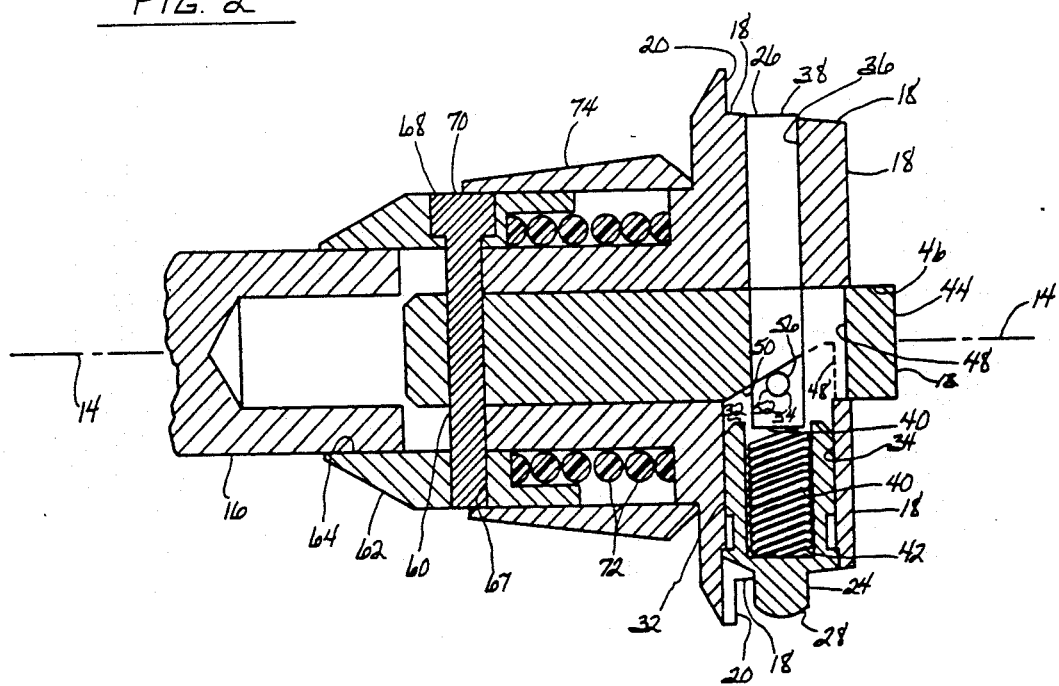
FIG. 3 is a view similar to that shown in FIG. 2 showing the action pin in its retracted position and the actuator in its extended position.

The tool driver 10 of the invention grips the base 12 of an acetabular reamer cup or other tool 15 at front end 13 and is clasped by a chuck or other holder of a portable drill or rotary shaft (not shown) at the rear end 30. Tool driver 10 has a longitudinal axis 14 and an elongated body 16. Body 16 as shown in FIGS. 1–3 has a boss 18 at end 13 surrounded by a flange 20 which extends generally perpendicularly of axis 14 outwardly of boss 18. Boss 18 is generally frusto-conical in shape, tapering from end 13 outwardly toward end 30. Flange 20 extends from the base of boss 18 radially outwardly of body 16.

Boss 18 is shaped and sized to receive thereon a tool 12 which has an open base 12. Base 12 fits over boss 18 with its peripheral edge against flange 20. Tool 15 is provided with diametrically opposite openings 22 therein through which pins 24 of tool driver 10 are positioned to secure tool 15 onto tool driver 10 with boss 18 within the reamer cup.

Pins 24 and 26 extend in diametrically opposite directions from boss 18 radially outwardly of tool driver 10. As shown in FIGS. 2 and 3, pin 24 is provided with a distal end 28 and a threaded end 32. Threaded end 32 is positioned within a threaded opening 34 within boss 18. Latch pin 26 is positioned within a bore 36 in boss 18. Bore 34 and bore 36 are coaxial on opposite sides of axis 14. Latch pin 26 has a distal end 38. Pin 24 has an interior bore 40 therein in which a spring 42 is positioned. Spring 42 extends from within pin 24 to abutment end 40 of latch pin 26.

Latch pin 26, thus, can move within bore 34 between its retracted position as shown in FIG. 3, and its extended position as shown in FIG. 2 against spring 40. Providing limits for movement of latch pin 26 is the action pin 44.

Action pin 44 is positioned within an axially extending bore 46 which extends from end 13 into shaft body 16. Action pin 44 is positioned within bore 46 and has a transversely extending bore 48 extending therethrough in which latch pin 26 is positioned. Bore 48 has an axial length of twice the diameter of latch pin 26 and a dimension transverse thereto of at least the diameter of latch pin 26. Thus, action pin 44 can move axially of both boss 18 and shaft body 16 a distance equal to at least two diameters of latch pin 26 without engaging latch pin 26.

Action pin 44 further has a stop surface 48 and a cam surface 50 thereon adjacent end 40. Stop surface 48 extends longitudinally of latch pin 26 inwardly from end 40. In the specific embodiment shown, stop surface 48 is planar and extends from side to side of action pin 44 and half way through action pin 44. Cam surface 50 also is planar and extends side to side of action pin 44, but is angularly disposed both to the axis of action pin 44 and stop surface 48. Cam surface 50 slopes outwardly of pin 44 away from end 13.

Latch pin 26 is provided with a bore 52 and a pin 54 which extends through the bore 52 radially outwardly of latch pin 26 on both sides thereof. Pin 54 has cylindrical cam surfaces 56 thereon exterior of latch pin 26. Cam surface 56 engages cam surface 50 of action pin 44 during the movement of action pin 44 axially of boss 18 and shaft body 16. This movement of the cam surfaces 50, 56 of pin 44 and 54 between opposite engagements of latch pin 26 and action pin 44 moves latch pin 26 between its retracted position and its extended position and expands and compresses spring 42.

A bore 58 of similar size to bore 48 is provided through shaft body 16 at a position spaced from end 13. Bore 58 extends through shaft body 16. Similarly, a bore 60 of a diameter generally half or less than half of the actual dimension of bore 58 is positioned remotely from bore 48 and extends through action pin 44.

A thumb trigger, or collar 62 is provided to slide on shaft body 16. Thumb trigger 62 has a bore 64 therein in which shaft body 16 is positioned. Thumb trigger 62 also has a bore 66 extending therethrough which is generally of the same size as bore 60, but with one end 67 having threads and the other end 68 being counterbored to receive the head of a pin 70. Pin 70 extends through thumb trigger 62 through bore 60 of action pin 44 and is held in place by threaded end 66 and complementary threads on pin 70. Thus, pin 70 connects together actuator action pin 44 and thumb trigger 62. Thumb trigger 62 and action pin 44 and pin 70 thus can move relative to shaft body 16 over the limits of bores 48 and 58. In a particular embodiment, the limits to the movement of action pin 44 and thumb trigger 62 are the axial limits of bore 48. In another particular embodiment, the limits of movement of action pin 44 and thumb trigger 62 are the axial limits of bore 58.

A helical spring 72 is positioned between boss 18 of body 16 and thumb trigger 62 to urge thumb trigger 62 into its rearward position as shown in FIG. 2.

Thumb trigger 62 and action pin 44 can be moved toward end 13 against the compression of spring 72. Overlaying spring 72 and thumb trigger 62 and extending between thumb trigger 62 and boss 18 of body 16 is a sleeve 74 which remains stationary with respect to shaft body 16. Sleeve 74, both cosmetically and functionally, covers spring 72 such that spring 72 is not exposed to the exterior of tool driver 10 and is shielded from debris.

Alternate embodiments of the tool driver of the invention are illustrated in FIGS. 1–3. In FIG. 1, latch pin 26 has calming surfaces at end 40 and action pin 44 has its camming surface 50 and its stop 48 oppositely facing that shown in FIGS. 2 and 3. In the embodiment of FIG. 1, end 40 itself rides upon camming surface 50, to move latch pin 26 from its retracted position to its extended position.

Figure 4:
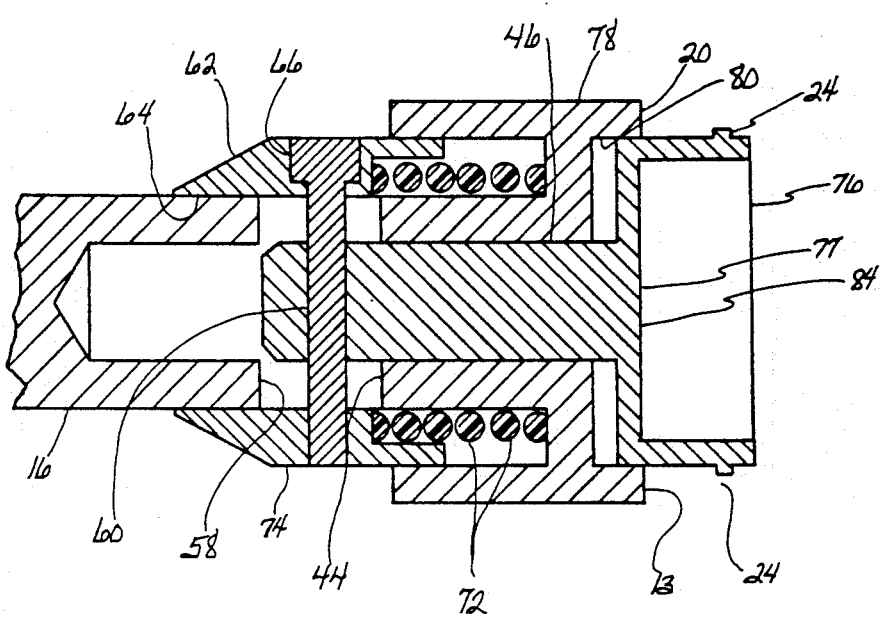
FIG. 4 is a view similar to that of FIGS. 2 and 3 showing yet another tool driver of the invention in which the boss is replaced with a cavity in which a plunger on the actuator pin is positioned.

In another embodiment, tool driver 10 of the invention is provided with a plunger 76 secured to the end 77 of action pin 44 adjacent end 13. Referring to FIG. 4, shaft body 16 is provided with a boss 78 in which a cavity 80 is positioned at end 13. Cavity 80, in a particular embodiment, is a cylindrical bore coaxial of boss 78 and shaft body 16. In that same particular embodiment, plunger 76 is also cylindrical and complementary to cavity 80 such that it fits into cavity 80 when thumb trigger 62 is in its most rearward position in sliding relationship. Plunger 76 is provided with radially extending diametrically opposed pins 24. These pins are stationary pins like pin 24 above described.

Figure 5A:
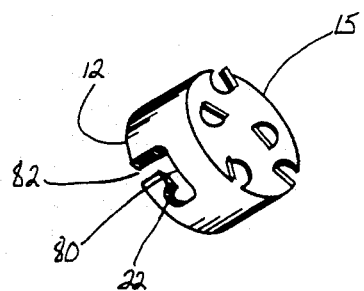
FIG. 5, A, B, and C illustrates in perspective tools for use with the tool driver shown in FIG. 4.
Figure 5B:
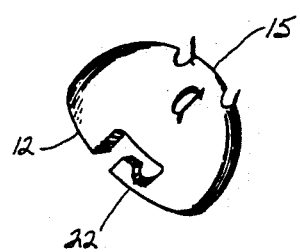
Figure 5C:
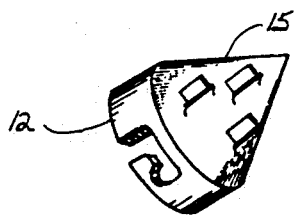

The tools for use with the tool driver 10 having the plunger 76 are like the tools above described, each provided with oppositely disposed, diametrical pin openings 22. However, each is also provided with diametrically opposite channels 80 having entrance openings 82 in which pins 24 can be positioned and caused to move so as to position pins 24 in pin openings 22. These tools, shown in three of the various configurations, in FIG. 5 are in a wide variety of tool configurations.

In a preferred embodiment, plunger 76 is provided with a debris cup 84 therein. In some applications, it is desirable to collect bone debris for placement between a new implant and the milled portion of the bone to assist healing. In such applications, a plunger with a debris cup 84 is utilized such that debris may be collected for this use.

In operation, the tool driver 10 of the invention can be utilized to tightly grip and easily release a tool such as an acetabular reamer cup which has an open end 12 shaped complementary to boss 18 or plunger 76 and which has diametrically opposite openings for the reception of pins 24 and 26 single handedly. In order to position such a tool on the tool driver 10, the tool is positioned on boss 18 or plunger 76, and thumb trigger 62 is moved against the urging of spring 72 toward end 13.

The movement of thumb trigger 62 as shown in FIGS. 1-3 towards end 13 moves action pin 44 axially of the shaft body 16 so as to extend from boss 18, and moves pin 54 on cam surface 50, thereby retracting latch pin 26. With the thumb trigger held in its most forward position, with latch pin 26 fully retracted, one of the pin holes in the tool is positioned around stationary pin 28 and the diametrically opposite portion of the tool is positioned against flange surface 20. Thumb trigger 62 is then released upon which spring 72 urges thumb trigger 62 and action pin 44 into its most rearward position as defined by the axial limits of either bore 58 as above mentioned. When thumb trigger 62 is in its most rearward position, latch pin 26 is extended from boss 18 and both pins 26 and 28 are positioned in the diametrically opposite pin holes of tool 12. Disassembly of tool 12 from the tool driver 10 can be accomplished by the reverse of these actions.

Referring to FIG. 4, tool driver 10, as shown therein, similarly functions. By urging the thumb trigger 62 toward end 13, plunger 76 is moved out of its at rest position within cavity 80. By this movement, pins 24 are moved away from end 13 of boss 78. In this position, a tool can be placed over the plunger 76, and pins 24 can be placed within the channel entrances 82 and the tool rotated so as to move the pins through channel 80 and into pin openings 22. Thumb trigger 62 is then released and spring 72 urges thumb trigger 62 into its rearward position and plunger 76 is retracted into cavity 80 thereby urging pins 24 toward boss 78 thereby resiliently securing the tool against end 13.

It will be noted that all of the moving parts which are exposed to the exterior of tool driver 10 are shielded for the most part by sliding tolerances from debris. All of the intricate parts, such as spring 42 and the like, are enclosed within tool driver 10 and are not exposed to debris. Further, those surfaces which are most likely to collect debris are either smooth exposed surfaces or surfaces like bore 34, bore 46, the exterior surface of shaft body 16 adjacent thumb trigger 62, the exterior surface of thumb trigger 62 itself, each of which may collect debris, but which are, in essence, self-cleaning by the movement of pins 26, 44 and thumb trigger 62 as above described.

Cleaning of most of the surfaces likely to collect debris can be accomplished easily without disassembly by washing the exterior of tool driver 10 and moving thumb trigger 62 between its most forward and most rearward positions.

If more thorough cleaning is required, the tool driver 10 can be completely disassembled, piece by piece, by removing pin 70 from the tool driver 10 and disassembling the same.

By the invention, an improved pin type tool driver of the invention is provided. The improved tool driver of the invention tightly grips and easily releases pin type tools single handedly. The tool driver of the invention is provided with moving parts which do not tend to collect bone debris. Additionally, the tool driver of the invention can be cleaned without disassembly, and can be easily disassembled for thorough cleaning if desired.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a body having a longitudinal axis and opposite ends, a boss at one of said ends, a tool collet at the other of said ends, a first bore in said body extending axially thereof, a plunger positioned within said bore, a pair of oppositely disposed pins, at least one of said pins being movable in relation to said body in response to movement of said plunger, an actuator on said body, said actuator connected to said plunger, said actuator and plunger movable as a unit axially of said body between an at rest position and a static position, said at least one pin being movable between an extended position and a retracted position, said at least one pin being in said extended position when said plunger and actuator are in said at rest position, said at least one pin being in its retracted position when said plunger and actuator are in its static position, whereby a tool can be positioned on said tool driver when said plunger and actuator are in their static position and held in operable position on said tool driver when said plunger and actuator are in said at rest position.

2. The tool driver of claim 1 wherein said body and actuator and plunger each have a bore extending therethrough, a pin positioned in said bores and secured to said actuator and plunger, said body bore having a dimension axially of said body about twice the diameter of said pin, whereby said actuator and plunger can move axially of said body as a unit a distance equal to about twice the diameter of said pin.

3. The tool driver of claim 1 wherein a spring is positioned and compressed between said body and said actuator, whereby said actuator and plunger are urged into their at rest position.

4. The tool driver of claim 1 wherein a spring is positioned around said body and compressed between said body adjacent said one end and said actuator whereby said actuator is urged into its at rest position.

5. The tool driver of claim 1 further comprising a sleeve extending from adjacent said one end and over said spring and a portion of said actuator whereby said spring is shielded from debris and said actuator is essentially in a self-cleaning and sliding relation with said body and sleeve.

6. The tool driver of claim 1 wherein said body has a boss at said one end, and said pins extend from said boss radially outwardly of said boss and said body, said at least one pin being biased radially outwardly, said at least one pin having camming surfaces thereon, said plunger having camming surfaces thereon which are in contact with said pin camming surfaces, said camming surfaces both having an at rest position and sloping away from said one end and said at rest position of said camming surfaces, whereby said pin is retracted into said boss upon moving said plunger toward said one end.

7. The tool driver of claim 6 wherein said camming surfaces face said at least one pin, and said camming surfaces slope away from said one end and toward said pin.

8. The tool driver of claim 6 wherein said camming surfaces face away from said at least one pin and said camming surfaces slope away from both said one end and said pin.

9. The tool driver of claim 6 wherein said pin is positioned in a bore in said boss, said boss and said pin being in essentially a self-cleaning, sliding relation with each other.

10. The tool driver of claim 6 wherein said pin is positioned in a bore extending through said plunger, said pin camming surface being on a pin extending from said pin, said spring urging said pin to move in said boss and plunger bores, said camming surfaces and spring being shielded from debris by said boss and plunger.

11. The tool driver of claim 6 wherein said boss has a flange surface spaced from said one end extending radially outwardly therefrom, said flange surface facing said one end, said pins extending from said boss spaced from said flange surface, whereby said pins can be positioned in complementary holes in a tool resting on said flange surface with said boss within a complementary tool interior, and said tool fastened to said tool driver thereby.

12. The tool driver of claim 1 wherein said body has a boss at said one end, said boss has a cavity extending thereinto from said one end, said plunger having an enlarged portion at its distal end, said enlarged portion being positioned in said cavity, said enlarged portion having said at least one pin extending radially therefrom, said pin being in said extended position adjacent said boss and being in said retracted position remote from said boss.

13. The tool driver of claim 12 wherein said boss and said enlarged portion are coaxial, said enlarged portion is smaller than said boss, and said pins overlay said boss.

14. The tool driver of claim 12 wherein said enlarged portion and said cavity are complementary, said enlarged portion and said cavity fit together in essentially a self-cleaning, sliding relation.

15. The tool driver of claim 12 wherein said enlarged portion has a debris cavity therein.

16. The tool driver of claim 12 further comprising a tool and wherein said tool overlays said debris cavity and has opposite openings therein in which said pins are positioned, said openings being spaced from the perimeter of said tool a distance greater than the distance between said pins and said boss when said enlarged portion is in said at rest position, whereby said pins urge said tool against said boss and said tool is fastened to said tool driver by said pins.

17. The tool driver of claim 1 further comprising a tool having opposed openings therein, said pins being positioned in said openings, thereby fastening said tool to said tool driver.

18. The tool driver of claim 17 wherein said tool has a cutting surface chosen from the group of cutting surfaces consisting of planar surfaces, conical surfaces, and spherical surfaces.

* * * * *